United States Patent
Nakagawa et al.

(10) Patent No.: US 10,330,599 B2
(45) Date of Patent: Jun. 25, 2019

(54) CALIBRATION CURVE DETERMINATION METHOD, CARBON CONCENTRATION MEASUREMENT METHOD, AND SILICON WAFER-MANUFACTURING METHOD

(71) Applicant: GlobalWafers Japan Co., Ltd., Niigata (JP)

(72) Inventors: Satoko Nakagawa, Tokyo (JP); Yuta Nagai, Tokyo (JP)

(73) Assignee: GlobalWafers Japan Co., Ltd., Niigata (JP)

( * ) Notice: Subject to any disclaimer, the term of this patent is extended or adjusted under 35 U.S.C. 154(b) by 0 days.

(21) Appl. No.: 15/850,467

(22) Filed: Dec. 21, 2017

(65) Prior Publication Data

US 2018/0231468 A1 Aug. 16, 2018

(30) Foreign Application Priority Data

Feb. 10, 2017 (JP) ................................ 2017-022927

(51) Int. Cl.
*G01N 21/64* (2006.01)
*G01N 1/30* (2006.01)
(Continued)

(52) U.S. Cl.
CPC ........... *G01N 21/6489* (2013.01); *G01N 1/30* (2013.01); *G01N 21/645* (2013.01);
(Continued)

(58) Field of Classification Search
CPC .............. G01J 3/4406; G01N 21/6489; G01N 21/9501; H01L 22/10
See application file for complete search history.

(56) References Cited

U.S. PATENT DOCUMENTS 9,541,452 B2   1/2017  Nakagawa et al.
2014/0021344 A1 1/2014  Okada et al.
(Continued)

FOREIGN PATENT DOCUMENTS

CN     103477207 A     12/2013
JP     H04-104042 A     4/1992
(Continued)

OTHER PUBLICATIONS

M. Nakamura, et al., "Photoluminescence Measurement of Carbon in Silicon Crystals Irradiated with High Energy Electrons", The Electrochemical Society, Inc., vol. 141, No. 12, Dec. 1994, pp. 3576-3580 (5 pages).
(Continued)

*Primary Examiner* — Yara B Green
(74) *Attorney, Agent, or Firm* — Harness, Dickey & Pierce, P.L.C.

(57) ABSTRACT

A carbon concentration can be measured using a small number of calibration curves even for a silicon wafer containing oxygen at a high concentration. A calibration curve determination method includes determining calibration curves using data sets each including a plurality of data, each data including irradiation dose, oxygen concentration, carbon concentration, and luminescence intensity, the data of each data set having the same irradiation dose and the same oxygen concentration, and the data sets being different in at least one of the irradiation dose and the oxygen concentration, selecting one or more combinations each being a pair of the calibration curves which are equal to each other in the irradiation dose and different from each other in the oxygen concentration, and obtaining a difference between slopes of the paired calibration curves on a log-log plot for each combination.

10 Claims, 7 Drawing Sheets

(51) Int. Cl.
*H01L 29/16* (2006.01)
*H01L 29/36* (2006.01)
*H01L 21/66* (2006.01)
*G01N 21/95* (2006.01)

(52) U.S. Cl.
CPC ......... *G01N 21/9501* (2013.01); *H01L 22/12* (2013.01); *H01L 29/16* (2013.01); *H01L 29/36* (2013.01); *G01N 2201/12746* (2013.01)

(56) References Cited

U.S. PATENT DOCUMENTS

2015/0338276 A1 11/2015 Nakagawa et al.
2016/0300768 A1* 10/2016 Kamada ............... G01N 27/041

FOREIGN PATENT DOCUMENTS

| | | |
|---|---|---|
| JP | 2013-152977 A | 8/2013 |
| JP | 2015-101529 A | 6/2015 |
| JP | 2015-156420 | 8/2015 |
| KR | 20140058587 | 5/2014 |

OTHER PUBLICATIONS

Taiwanese Office Action for TW Application No. 106141698, dated Nov. 12, 2018 (5 pages).
Office Action for Korean application 9-5-2019-005262775, dated Jan. 22, 2019 (with English translation); 18 pages.
Office Action for Korean application 2017-0179436, dated Jan. 22, 2019 (with English translation); 18 pages.

\* cited by examiner

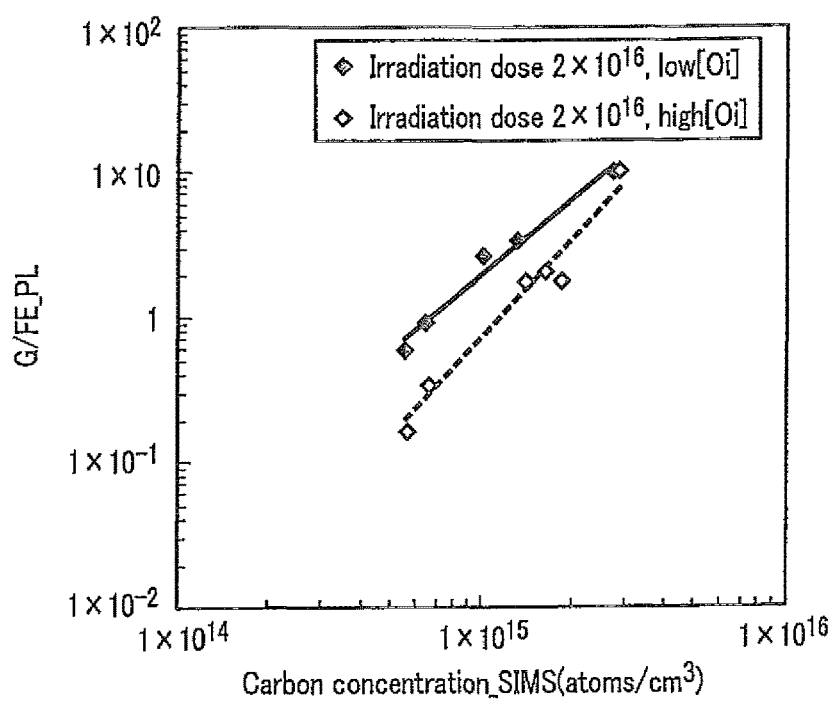
F I G. 6
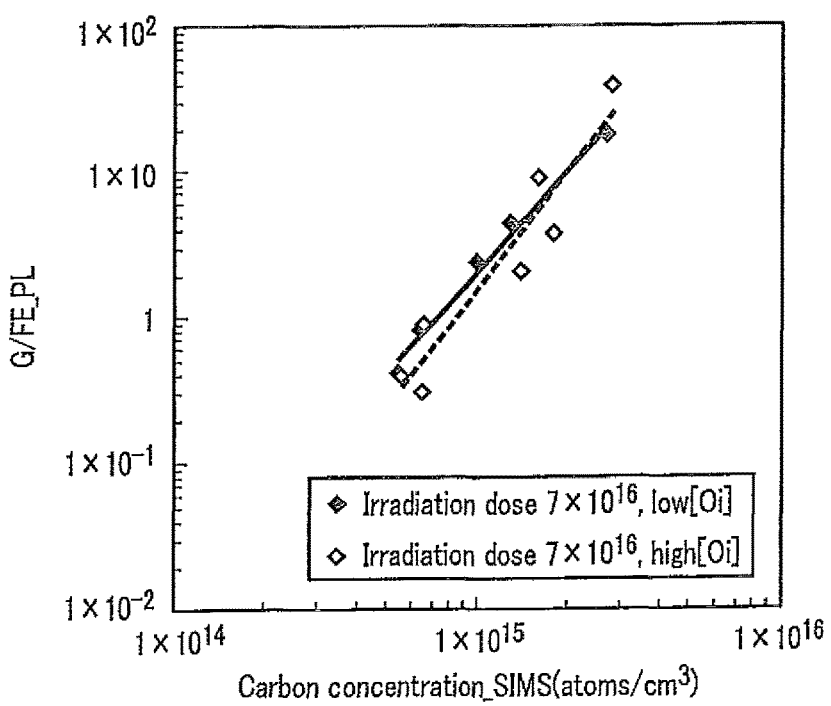
F I G. 7

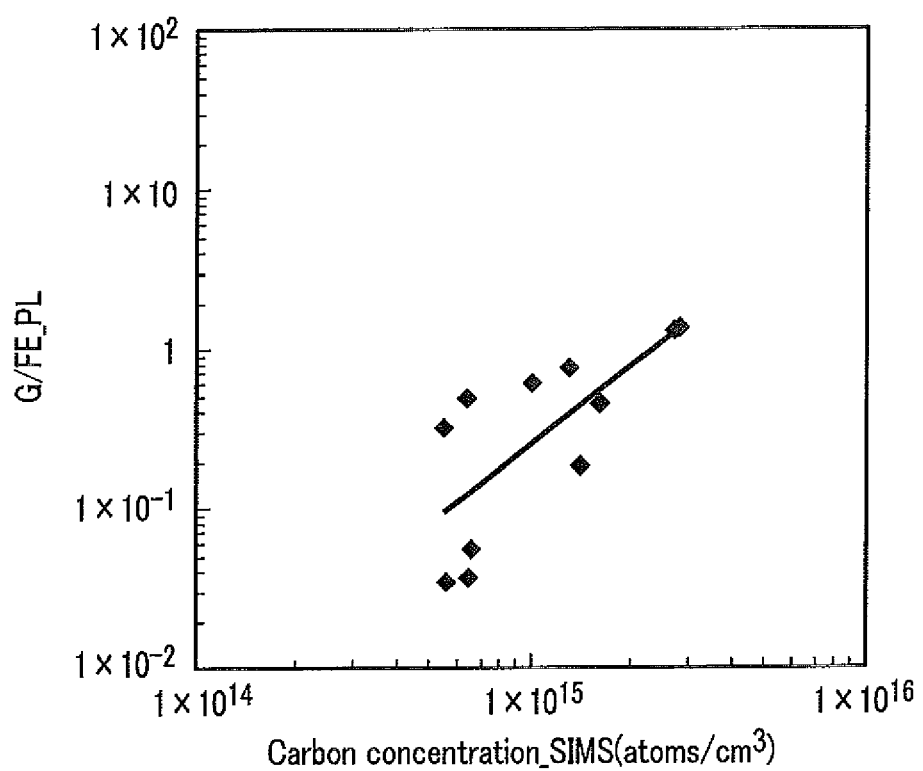
F I G. 10

CALIBRATION CURVE DETERMINATION METHOD, CARBON CONCENTRATION MEASUREMENT METHOD, AND SILICON WAFER-MANUFACTURING METHOD

CROSS-REFERENCE TO RELATED APPLICATIONS

This application is based upon and claims the benefit of priority from Japanese Patent Application No. 2017-022927, filed Feb. 10, 2017, the entire contents of which are incorporated herein by reference.

FIELD

The present invention relates to a calibration curve determination method, a carbon concentration measurement method, and a silicon wafer-manufacturing method.

BACKGROUND

In recent years, energy savings and shifts to clean energy have advanced. Along with these, a power device market scale has increased.

For manufacturing power devices, a silicon wafer is used, for example. Such a silicon wafer preferably contains almost no impurity including carbon and oxygen. Contamination of the silicon wafer with impurities is, however, inevitable in the manufacturing process thereof. For this reason, it is important to know the concentrations of impurities contained in the silicon wafer.

A silicon single-crystal having desirable characteristics for a power device substrate has a carbon concentration equal to or lower than the lower quantitation limit of secondary ion mass spectrometry (SIMS), which is a known measurement method. Thus, it had been difficult to accurately determine the carbon concentration in such a silicon single-crystal. Under these circumstances, a measurement method using a photoluminescence (PL) method was proposed as a method of measuring a low carbon concentration. The PL method is a method which includes irradiating a material with excitation light and observing light emitted when the transition of the excited electrons to the ground state occurs.

Jpn. Pat. Appin. KOKAI Publication No. 2013-152977 describes a method of measuring a concentration of an impurity in a semiconductor wafer using the PL method. According to this method, the semiconductor wafer is irradiated with an electron beam to render the impurity contained in the semiconductor wafer luminescence-active, and then the luminescence intensity is measured by the PL method. A ratio of the intensity at 1,280 nm to the intensity at 1,570 nm is obtained from the spectrum. A calibration curve representing the relationship between the luminescence intensity ratio thus obtained and the concentration of the impurity contained in the semiconductor wafer is then determined. Thereafter, the calibration curve is extrapolated to a lower carbon concentration range, and the measurement of the luminescence intensity is performed on a wafer containing an impurity at a low concentration. This luminescence intensity is referred to the calibration curve to obtain the impurity concentration.

Jpn. Pat. Appin. KOKAI Publication No. 2015-101529 describes a carbon concentration measurement method by which the influence of the oxygen concentration on a measurement result is small. According to this method, luminescence intensity ratios obtained using the PL method and concentration division values, which are ratios of carbon concentrations to oxygen concentrations, are obtained for a plurality of silicon single-crystals having different carbon and oxygen concentrations. A calibration curve representing the relationship between the photoluminescence ratios and the concentration division values is determined. Thereafter, the luminescence intensity measurement is performed on a silicon single-crystal specimen, and the measurement results are referred to the calibration curve to obtain the concentration division value. Subsequently, the oxygen concentration of a silicon single-crystal specimen is measured, and the carbon concentration is calculated from the oxygen concentration and the concentration division value.

SUMMARY

When intensity of luminescence deriving from carbon is obtained by the PL method, the concentration of oxygen contained in a silicon wafer has influence on the intensity. For this reason, in order to measure carbon concentrations of a plurality of silicon wafers containing oxygen at different oxygen concentrations by using the method described in Jpn. Pat. Appin. KOKAI Publication No. 2013-152977, calibration curves must be determined for respective oxygen concentrations.

Jpn. Pat. Appin. KOKAI Publication No. 2015-101529 uses, as one parameter of the calibration curve, a concentration division value which is the ratio of a carbon concentration to an oxygen concentration. This makes it possible to obtain the carbon concentrations even in the case where the silicon single-crystals have different oxygen concentrations.

The present inventors, however, found that when the carbon concentration of a silicon wafer containing oxygen at a high concentration is to be measured using the calibration curve in Jpn. Pat. Appin. KOKAI Publication No. 2015-101529, the influence of the oxygen concentration cannot be eliminated. For example, an ingot produced by the Czochralski method tends to contain oxygen at a high concentration. A silicon wafer obtained from such an ingot contains oxygen at a higher concentration as compared with an oxygen concentration range ($1\times10^{17}$ to $8\times10^{17}$ atoms/cm$^3$) used for determining a calibration curve in Jpn. Pat. Appin. KOKAI Publication No. 2015-101529. In this case, even by the method of Jpn. Pat. Appin. KOKAI Publication No. 2015-101529, the influence of the oxygen concentration on the result of the measurement performed on the carbon concentration cannot be eliminated, and calibration curves must be determined for respective oxygen concentrations.

In consideration of the above situation, an object of the present invention is to make it possible to measure a carbon concentration using a small number of calibration curves even for a silicon wafer containing oxygen at a high concentration.

According to a first aspect of the present invention, there is provided a calibration curve determination method comprising: a first step of providing a plurality of wafer groups each including a plurality of silicon wafers having the same oxygen concentration and different carbon concentrations, the wafer groups being different from each other in the oxygen concentration of the silicon wafers included therein; a second step of irradiating a plurality of regions of each of the silicon wafers included in each of the wafer groups with electron beams at different irradiation doses; a third step of obtaining, by a photoluminescence method, an intensity ratio of a first luminescence intensity deriving from silicon to a second luminescence intensity deriving from carbon for each of the regions irradiated with the electron beams; a fourth step of classifying a plurality of data each including the oxygen concentration, the carbon concentration, the irradiation dose, and the intensity ratio into a plurality of data sets, the data included in each of the data sets having the same irradiation dose and the same oxygen concentration, and the data sets being different from each other in at least one of the irradiation dose and the oxygen concentration, and determining a first calibration curve representing a relationship between the intensity ratio and the carbon concentration for each of the data sets to obtain a calibration curve group; a fifth step of selecting one or more combinations from the calibration curve group, each of the one or more combination being a pair of first calibration curves which are equal to each other in the irradiation dose and different from each other in the oxygen concentration, and the one or more combinations being different from each other in the irradiation dose, and obtaining a difference between slopes of the paired first calibration curves on a log-log plot for each of the one or more combinations; and a sixth step including selecting a specific combination out of the one or more combinations, the specific combination having the difference between the slopes within a predetermined range or smaller than the difference between the slopes of one or more of other combinations, determining the irradiation dose in common to the first calibration curves of the specific combination as an electron beam irradiation dose for measurement, and determining a second calibration curve using all the data included in pair(s) of the data sets used to determine the pair(s) of first calibration curves included in at least the specific combination, the second calibration curve representing a relationship between the intensity ratio and the carbon concentration and being usable in combination with the electron beam irradiation dose for measurement.

According to a second aspect of the present invention, there is provided a carbon concentration measurement method comprising: determining the electron beam irradiation dose for measurement and determining the second calibration curve by the determination method according to the first aspect; irradiating a silicon wafer for measurement whose carbon concentration is unknown with an electron beam at the electron beam irradiation dose for measurement; obtaining, by a photoluminescence method, an intensity ratio of a first luminescence intensity deriving from silicon to a second luminescence intensity deriving from carbon for the silicon wafer for measurement irradiated with the electron beam; and referring the intensity ratio thus obtained to the second calibration curve to obtain a carbon concentration of the silicon wafer for measurement.

According to a third aspect of the present invention, there is provided a silicon wafer-manufacturing method comprising measuring a carbon concentration in the silicon wafer for measurement by the measurement method according to the second aspect.

BRIEF DESCRIPTION OF THE DRAWINGS

FIG. 6 is a log-log plot showing an example of a relationship between a carbon concentration and a luminescence intensity ratio when a calibration curve determination sample is irradiated with an electron beam at an irradiation dose of $2 \times 10^{16}$ electrons/cm$^2$;

FIG. 7 is a plot showing an example of a relationship between a carbon concentration and a luminescence intensity ratio when a calibration curve determination sample is irradiated with an electron beam at an irradiation dose of $7 \times 10^{16}$ electrons/cm$^2$;

FIG. 10 is a log-log plot showing an example of a second calibration curve according to Comparative Example 1.

DETAILED DESCRIPTION

Embodiments of the present invention will be described below. The following description does not intend to limit the present invention.

<<Calibration Curve Determination Method>>

Figure 1:
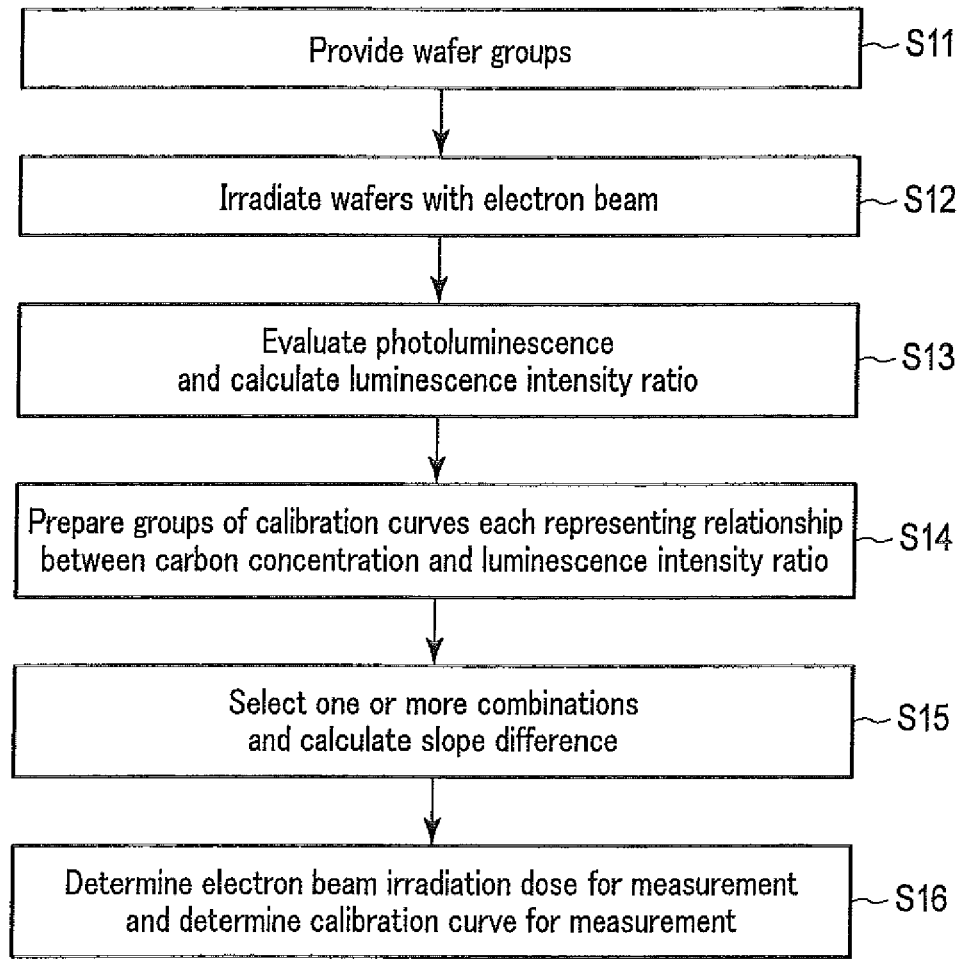
FIG. 1 is a flowchart showing a calibration curve determination method according to an embodiment of the present invention.

FIG. 1 is a flowchart showing a calibration curve determination method according to an embodiment of the present invention. In this method, a first step S11, a second step S12, a third step S13, a fourth step S14, a fifth step S15, and a sixth step S16 are performed in this order.

In the method shown in FIG. 1, a calibration curve is determined using a PL method. Prior to a detailed description of the method in FIG. 1, the principle of the PL method will be described below.

The PL method is a conventionally known method which includes irradiating a material with excitation light to cause excitation of electrons, and observing light emitted when the transition of the excited electrons to the ground state occurs. More specifically, electron-hole pairs are generated when a silicon wafer is irradiated with light having energy higher than that of the forbidden band. Here, an excess amount of electron-hole pairs with respect to a thermal equilibrium state are generated in silicon crystals. The excess electron-hole pairs recombine to recover an equilibrium state. Light is emitted in this recombination process. An impurity or defect in the silicon wafer can affect the spectrum of this emitted light. Therefore, information regarding impurities in the silicon wafer can be obtained by spectroscopically analyzing the light emission in detail.

In carbon impurity evaluation, when a silicon wafer is irradiated with an electron beam prior to irradiation with excitation light, the carbon impurity in this crystal is rendered luminescence-active. More specifically, when the silicon wafer is irradiated with the electron beam, irradiation damage or defects occur in the silicon crystal as follows:

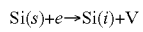

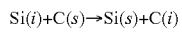

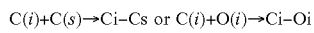

where V represents a vacancy, and e represents an electron. The suffix (s) represents that the atom immediately preceding this suffix is positioned at a lattice point (substitutional). The suffix (i) represents that the atom immediately preceding this suffix is positioned between lattice points (interstitial). That is, C(i) represents interstitial carbon, C(s) represents substitutional carbon, and O(i) represents interstitial oxygen. Also, Ci-Cs represents a complex defect of interstitial carbon and substitutional carbon, and Ci-Oi represents a complex defect of interstitial carbon and interstitial oxygen.

Thus, an introduction of the primary defects leads to generation of the Ci-Oi and Ci-Cs complex defects. These Ci-Oi and Ci-Cs defects emit light when irradiated with excitation light, more specifically, a laser beam such as visible light or ultraviolet light. The intensity or intensity ratio of the light emitted by these defects is influenced by, e.g., the number of Ci-Oi and Ci-Cs defects. Therefore, analyzing the luminescence intensity or intensity ratio can obtain information about a carbon impurity in the silicon wafer.

The method shown in FIG. 1 will be described in order of steps.

<First Step>

The first step S11 is a step of providing a plurality of wafer groups.

Each of the wafer groups includes a plurality of silicon wafers having the same oxygen concentration and different carbon concentrations. The wafer groups are different from each other in the oxygen concentrations of the silicon wafers included therein.

Each of the wafer groups is provided as follows. A plurality of silicon wafers are cut from one or more silicon single-crystal ingots manufactured by, for example, the Czochralski method. The carbon concentrations and the oxygen concentrations of these silicon wafers are determined. Secondary ion mass spectrometry (SIMS) can be used as a method of determining the carbon concentration. Fourier transform infrared spectroscopy (FT-IR) can be used as a method of determining the oxygen concentration. Based on these measurement results, the silicon wafers are classified into the wafer groups.

The number of silicon wafers included in each of the wafer groups is two or more. The accuracy of the calibration curves is improved when the number of silicon wafers having different carbon concentrations is increased. The number of silicon wafers included in each of the wafer groups is preferably 3 or more, and more preferably 4 or more.

The carbon concentrations of the silicon wafers included in each of the wafer groups preferably fall within the range of $4 \times 10^{14}$ to $4 \times 10^{15}$ atoms/cm$^3$. If the carbon concentration is too low, the carbon concentration may not be determined by a measurement method other than the PL method. If the carbon concentration is too high, the amount of carbon contained in the silicon wafer is excessive, and electron beam irradiation cannot sufficiently cause luminescence-activation. Note that the luminescence-activation by electron beam irradiation will be described in detail later.

The number of wafer groups is 2 or more. When increasing the number of wafer groups which are different from each other in the oxygen concentration of the silicon wafers, the accuracy of the calibration curves is improved. The number of wafer groups is preferably 3 or more, and more preferably 4 or more.

The oxygen concentration of the silicon wafers included in each of the wafer groups preferably falls within the range of $1 \times 10^{17}$ to $2 \times 10^{18}$ atoms/cm$^3$ (ASTM '79). When the oxygen concentration is too low, and a silicon wafer for measurement, i.e., a silicon wafer on which the carbon concentration measurement using a calibration curve determined by the method described here is to be performed, has a relatively high oxygen concentration, the generation balance between G-line photoluminescence deriving from the Ci-Cs complex defect and C-line photoluminescence deriving from the Ci-Oi complex defect greatly differ between the measurement by the PL method performed in order to determine the calibration curve and the measurement by the PL method performed on the silicon wafer for measurement. As a result, there is a possibility that calibration curves need to be determined for respective oxygen concentrations. In the case where the oxygen concentration is too high, the amount of oxygen precipitates increases, which makes the Ci-Oi complex defect less prone to be generated as compared with the case where oxygen atoms are uniformly distributed in a silicon wafer. Accordingly, in such a case, when the oxygen concentration of the silicon wafer for measurement is relatively low, the generation balance between G-line photoluminescence and C-line photoluminescence greatly differs between the measurement by the PL method performed in order to determine the calibration curve and the measurement by the PL method performed on the silicon wafer for measurement. As a result, there is a possibility that the carbon concentration of the silicon wafer for measurement cannot be accurately measured.

The silicon wafers for determining calibration curves and the silicon wafer for measurement may contain a dopant in a concentration falling within the range in which a first luminescence intensity to be described later is measurable. The dopant is added to adjust the resistivity of a semiconductor. Examples of the general dopant are boron (B), phosphorus (P), aluminum (Al), and arsenic (As). These dopants can be detected as bound exciton luminescence (BE luminescence) in the measurement by the PL method. When the dopant concentration is too high, a peak deriving from the first photoluminescence is embedded in the tail of a peak deriving from BE luminescence. This may make it difficult to detect the first photoluminescence or impossible to detect it.

<Second Step>

The second step S12 is a step of irradiating a silicon wafer with an electron beam to render carbon contained in the silicon wafer luminescence-active. More specifically, a plurality of regions of each silicon wafer included in each of the wafer groups, which are provided in the first step S11, are irradiated with electron beams at different irradiation doses.

The electron beam irradiation doses preferably fall within the range of $1 \times 10^{14}$ to $1 \times 10^{18}$ electrons/cm$^2$. The electron beam irradiation doses more preferably fall within the range of $1 \times 10^{15}$ to $1 \times 10^{17}$ electrons/cm$^2$. When the irradiation dose of the electron beam is too low, carbon contained in the silicon wafer may not be sufficiently luminescence-activated. To the contrary, when the electron beam irradiation dose is too high, irradiation damage to the silicon wafer is large to increase the number of non-radiative centers, which cause no luminescence although having a defect level. As a result, a lower value may be detected as the luminescence intensity.

In the case where electron beam irradiation is performed at a sample temperature not exceeding 100° C., annealing out of the irradiation defect such as a vacancy introduced by electron beam irradiation, which causes restoration of the defect, can be suppressed as compared with the case where the electron beam irradiation is performed at a higher temperature. Examples of the irradiation method include a method in which the irradiation is performed under air-cooling and a method in which the irradiation is performed in the atmosphere while water-cooling an irradiation stage.

A particle beam other than the electron beam can be used for the luminescence-activation of an impurity such as carbon. For example, irradiation with a high-energy particle such as proton or various kinds of ions may be performed. In this case, however, not only are the atomic vacancies (V) introduced, but the generation of secondary defects such as vacancy clusters increase, as compared with the case of performing irradiation with an electron beam. Accordingly, when a silicon wafer containing a carbon impurity is irradiated with protons, photoluminescence other than that deriving from the carbon impurity increases. Examples of such photoluminescence, which are not found for electron beam irradiation, are photoluminescence deriving from interstitial silicon, photoluminescence deriving from crystal strain, and photoluminescence deriving from irradiation damage. In addition, the number of non-radiative centers increases. As a consequence, it becomes difficult to obtain an accurate correlation between the impurity concentration and luminescence intensity.

When performing PL measurement for a carbon impurity in a silicon wafer, therefore, an electron beam which can suppress photoluminescence irrelevant to carbon concentration evaluation and decrease the number of non-radiative centers is most suitably used for luminescence-activation. Electron beam irradiation is also preferable in allowing defects to be uniformly introduced in the depth direction.

Depending on the luminescence-activation condition, the luminescence intensity obtained by the PL method may be weaker immediately after the luminescence-activation process of the impurity than after certain period of time has lapsed from the luminescence-activation process. This is because many unstable irradiation defects which are restored at room temperature exist immediately after the luminescence-activation process. In this case, leaving the wafer at room temperature for a long period of time or annealing the wafer at a low temperature will increase the luminescence intensity. Note that annealing must be performed in a condition wherein defects contributing to carbon-related photoluminescence are not restored.

It is possible that the silicon wafer is singulated into pieces in advance, and then the electron beam irradiation is performed on the pieces. In the case of singulating the silicon wafer into pieces, each piece is prepared to have a size of, for example, 5 mm×10 mm.

<Third Step>

The third step S13 is a step of obtaining an intensity ratio of a first luminescence intensity deriving from silicon to a second luminescence intensity deriving from carbon for each of the regions irradiated with the electron beam.

Preferably, the first luminescence intensity is of free-exciton luminescence (FE luminescence), and the second luminescence intensity is of photoluminescence deriving from a complex defect of interstitial carbon and substitutional carbon. As the excitation light, for example, an excitation laser beam having a wavelength of 532 nm can be used.

According to the method shown in FIG. 1, for example, the G-line luminescence intensity is measured as the first luminescence intensity. Although the C-line luminescence also exists as a peak representing the carbon concentration, the C-line derives from Ci-Oi, which is formed of carbon and oxygen. To the contrary, the G-line derives from Ci-Cs, which is formed of only carbon. For this reason, the G-line luminescence exhibits a larger response change for a change in carbon concentration. Therefore, measuring the G-line luminescence allows the concentration of the carbon impurity to be measured more accurately.

The luminescence intensity is measured in a state in which, for example, a silicon wafer is immersed in a cryogenic liquid such as liquid helium and a temperature is kept constant. This allows to avoid generation of heat by a sample due to irradiation with the excitation laser beam and changes in a balance between various kinds of luminescence such as FE luminescence due to the fluctuations in sample temperature, and the measurement can be performed more stably.

<Fourth Step>

The fourth step S14 is a step of determining a first calibration curve representing the relationship between the carbon concentration and the luminescence intensity obtained by the PL method and obtaining a calibration curve group including a plurality of first calibration curves. More specifically, a plurality of data each including an oxygen concentration, a carbon concentration, an irradiation dose, and an intensity ratio are classified into a plurality of data sets. The data included in each of the data sets have the same irradiation dose and the same oxygen concentration. The data sets are different from each other in at least one of the irradiation dose and the oxygen concentration. A first calibration curve representing the relationship between the intensity ratio and the carbon concentration is determined for each data set to obtain a calibration curve group.

The "same oxygen concentration" indicates that the oxygen concentrations fall within the range of $0.5 \times C_O(Av)$ to $1.5 \times C_O$ (Av) where $C_O$ (A) is the average value of the oxygen concentrations. The "different value in oxygen concentration" indicates that the oxygen concentrations fall outside the above range.

The first calibration curve is a straight line obtained by plotting the logarithm of the luminescence intensity ratio with respect to the logarithm of the carbon concentration.

Letting [$G_{PL}/FE_{PL}$] be the ratio of the FE luminescence intensity to the G-line intensity, [C] be the carbon concentration, a be the slope on the plot of the luminescence intensity with respect to the carbon concentration, and A be the intercept on the log-log plot, the above relationship is given by the following equation (1).

$$[G_{PL}/FE_{PL}] = A \times [C]^a \quad (1)$$

The first calibration curve represented by equation (1) is determined for each of the data sets, thereby obtaining a calibration curve group including the first calibration curves.

<Fifth Step>

The fifth step S15 is a step of obtaining a difference between slopes for at least one combination selected from the calibration curve group. More specifically, one or more combinations are selected from the calibration curve group. Here, each of the one or more combinations is a pair of first calibration curves which are equal to each other in the irradiation dose and different from each other in the oxygen concentration, and the one or more combinations are different from each other in the irradiation dose. A difference between slopes of the paired first calibration curves on a log-log plot is obtained for each of the one or more combinations.

The slope of the calibration curve is the "a", which was referred in the fourth step S14. A pair of first calibration curves for obtaining the slope a can be arbitrarily selected. If two or more combinations which are different from each other in the irradiation dose are selected, this selection is arbitrary, too.

The pair of first calibration curves is preferably selected such that the difference in the slope is 0.5 or less. In selection of two or more combinations which are different in the irradiation dose, the first calibration curves included in each combination are preferably selected such that the difference in the slope is 0.5 or less. If the slope difference is too large, there is a possibility that the influence of the oxygen concentration on the result of the carbon concentration measurement cannot be eliminated, and thus it may be difficult to measure the carbon concentration with a small number of calibration curves.

<Sixth Step>

In the sixth step S16, an electron beam irradiation dose for measurement is determined, and a second calibration curve is determined.

More specifically, assume that the number of the combinations is 1. In this case, the slope difference is checked to fall within a predetermined range, for example, the range described in the fifth step S15. The irradiation dose in common to the first calibration curves of this combination is determined as the electron beam irradiation dose for measurement. Using all the data included in pair(s) of the data sets used to determine the pair(s) of first calibration curves included in at least this combination, a second calibration curve which represents a relationship between the intensity ratio and the carbon concentration and is usable under the electron beam irradiation dose for measurement is determined.

Alternatively, assume that the number of combinations is 2 or more. Among these combinations, selected is a specific combination having the slope difference which falls within a predetermined range, for example, the range described for the fifth step S15 or which is smaller than that of one or more other combinations. The irradiation dose in common to the first calibration curves of the specific combination is determined as the electron beam irradiation dose for measurement. Using all the data included in pair(s) of data sets used to form the pair(s) of first calibration curves included in at least this specific combination, a second calibration curve which represents the relationship between the intensity ratio and the carbon concentration and is usable under the electron beam irradiation dose for measurement is determined.

For determining the second calibration curve, it is possible to use, in addition to the data included in the above-described pair of data sets (to be referred to as data sets for determining the irradiation dose hereinafter), all the data included in one or more data sets (to be referred to as auxiliary data set hereinafter) whose irradiation dose is equal to those of the data sets for determining the irradiation dose and whose oxygen concentration falls between the oxygen concentration of the one of the data sets for determining the irradiation dose and the oxygen concentration of the other of the data sets for determining the irradiation dose. This makes it possible to increase the accuracy of the calibration curve.

The sixth step S16 may further includes calculating a correlation coefficient between the carbon concentration and the intensity ratio from all the data included in the data sets for determining the irradiation dose, and confirming that the second calibration curve can be used based on the correlation coefficient. Alternatively, in the case where the auxiliary data set is used to determine the second calibration curve, the sixth step may further includes calculating a correlation coefficient between the carbon concentration and the intensity ratio from all the data included in the data sets for determining the irradiation dose and the auxiliary data set, and confirming that the second calibration curve can be used based on the correlation coefficient.

The correlation coefficient can be obtained by the following equation (2).

$$R^2 = \frac{\left(\sum_{i=1}^{n}(xi-\bar{x})(yi-\bar{y})\right)^2}{\left(\sum_{i=1}^{n}(xi-\bar{x})^2\right)\left(\sum_{i=1}^{n}(yi-\bar{y})^2\right)} \quad (2)$$

$R^2$ is preferably 0.9 or more. In the case where $R^2$ is too small, the correlation between the carbon concentration and the intensity ratio is weak, and it may be difficult to measure a carbon concentration with a smaller number of calibration curves. This confirmation operation may be performed before or after the second calibration curve is determined.

If the magnitude of $R^2$ does not satisfy the standard, a calibration curve is determined for each oxygen concentration. Alternatively, the process may return to the fifth step S15 to select data sets for determining the irradiation dose again and determine a second calibration curve again.

The sixth step S16 may also include a process of extrapolating the determined second calibration curve to a lower carbon concentration range. This makes it possible to measure the carbon concentration of a silicon wafer for measurement containing carbon at a lower concentration than the carbon concentration used to form the calibration curve.

<<Carbon Concentration Measurement Method and Silicon Wafer-Manufacturing Method>>

Figure 2:
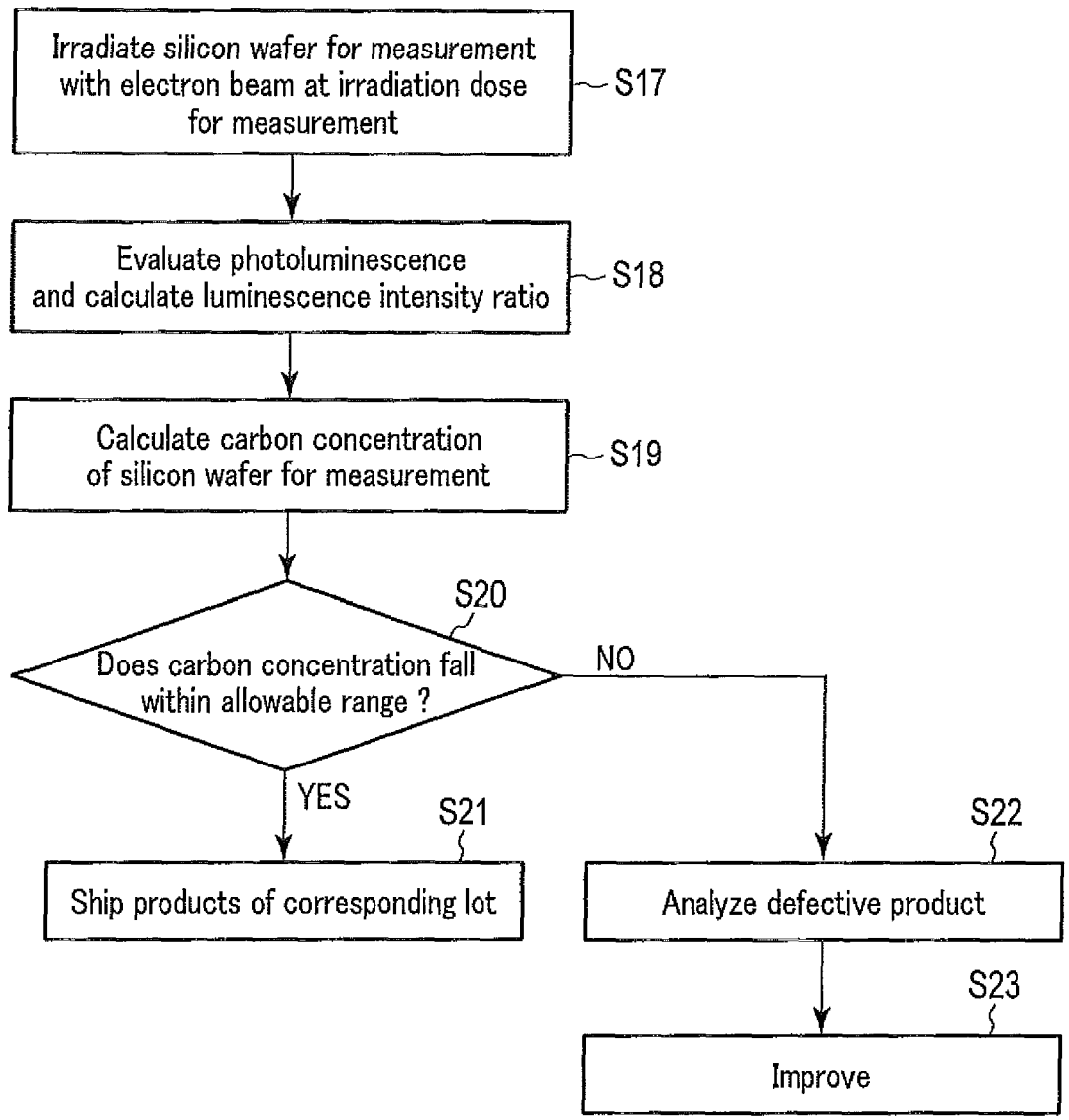
FIG. 2 is a flowchart showing a silicon wafer-manufacturing method according to an embodiment of the present invention.

FIG. 2 is a flowchart showing an example of a silicon wafer-manufacturing method including a method of measuring a carbon concentration using the calibration curve obtained by the method shown in FIG. 1. According to this manufacturing method, the seventh step S17, the eighth step S18, the ninth step S19, and the 10th step are executed in this order. Subsequently, according to this manufacturing method, based on the result of the 10th step S20, the 11th step S21 is performed or the 12th step S22 and the 13th step S23 are performed in this order.

The seventh step S17 is a step of irradiating a silicon wafer for measurement whose carbon concentration is unknown with an electron beam at the electron beam irradiation dose for measurement determined in the sixth step S16. The process, etc. of the electron beam irradiation method are preferably the same as the process, etc. employed to determine the calibration curve.

The eighth step S18 is a step of obtaining, by the PL method, the luminescence intensity ratio of a first luminescence intensity deriving from silicon to a second luminescence intensity deriving from carbon for a silicon wafer for measurement irradiated with an electron beam. This first luminescence is the same as the first luminescence measured at the time of determining the calibration curve. The first luminescence is, for example, FE luminescence. The second luminescence is the same as the second luminescence measured at the time of determining the calibration curve. The second luminescence is, for example, G-line luminescence. The wavelength or the like of excitation light used for measurement by the PL method is preferably the same as the wavelength or the like of excitation light used to form the calibration curve.

The ninth step S19 is a step of referring the luminescence intensity ratio obtained in the eighth step S18 to the second calibration curve to obtain the carbon concentration in the silicon wafer for measurement.

By executing the seventh step S17 to the ninth step S19, the concentration of carbon contained in the silicon wafer for measurement whose carbon concentration is unknown is obtained. This measurement method does not require complex concentration conversion.

The 10th step S20 is a step of determining whether the carbon concentration of the silicon wafer for measurement falls within a predetermined allowable range, for example, a predetermined range allowable for a silicon wafer as a product. The silicon wafer as the product is, for example, a power device substrate, a CMOS (complementary metal oxide semiconductor) image sensor substrate, or the like. A detailed example for determining whether a silicon wafer is nondefective or defective will be described using as an example a case in which this silicon wafer is used for a semiconductor device including a collector and an emitter.

First of all, the allowable range of a carbon concentration is determined. The allowable range of the carbon concentration is determined based on the allowable range of, for example, device characteristics such as switching characteristics and a collector-emitter saturation voltage. The carbon concentration of the silicon wafer influences the device characteristics about the lifetime characteristics. For example, the relationship between the carbon concentration of the silicon wafer and the device characteristics such as the collector-emitter saturation voltage is examined in advance. This makes it possible to determine the allowable range of the carbon concentration.

The carbon concentration of the silicon wafer for measurement is then obtained by the above measurement method. This carbon concentration is compared with the predetermined allowable carbon concentration range to determine whether the silicon wafer for measurement is nondefective or defective. For example, when the carbon concentration falls within the allowable range, the silicon wafer is determined as a nondefective wafer, and the 11th step S21 is performed. For example, the lot of such silicon wafers is shipped.

If the carbon concentration falls outside the allowable range, the wafer is determined as a defective wafer, and the 12th step S22 and the 13th step S23 are performed. For example, by analyzing the silicon wafer for measurement and confirming its manufacturing process conditions, the cause of the defect is analyzed. For example, the silicon wafer-manufacturing process is optimized.

As described above, according to this measurement method, the electron beam irradiation dose can be optimized. An example of the effect by the optimization of the electron beam irradiation dose is shown in FIG. 3.

Figure 3:
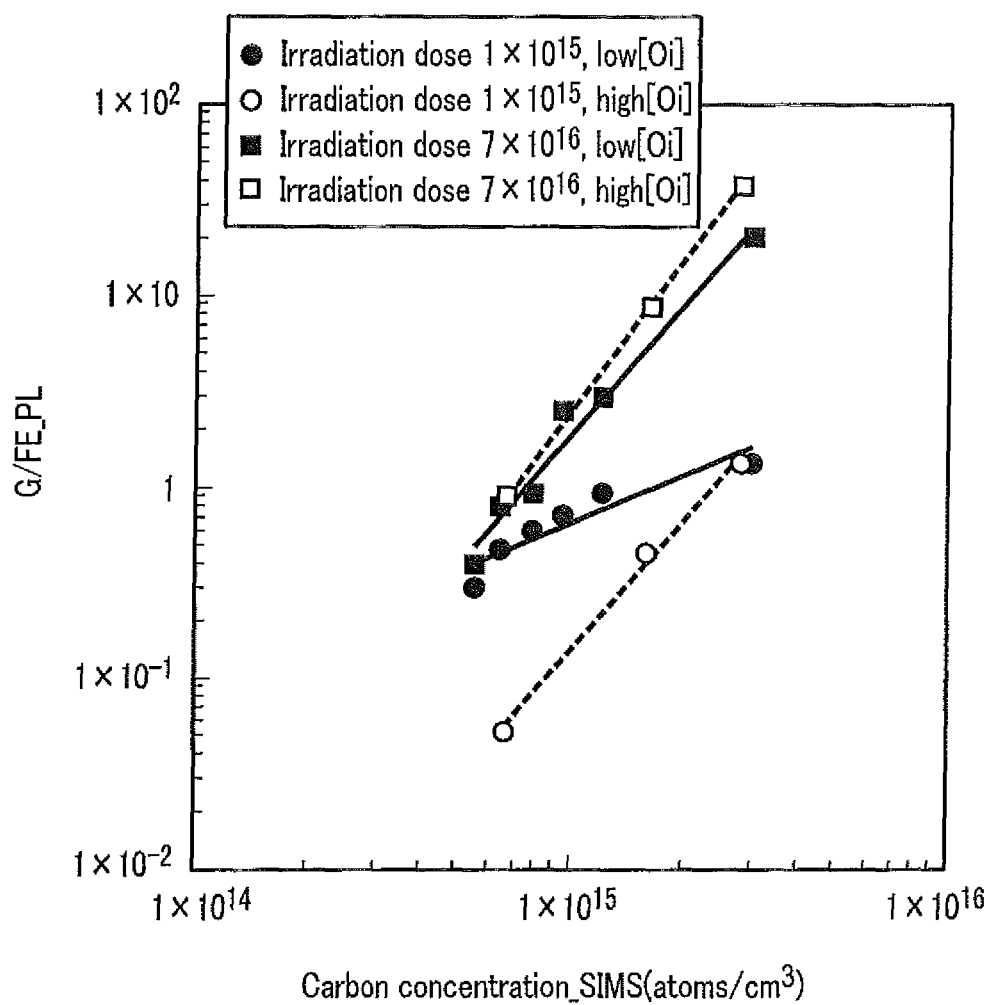
FIG. 3 is a graph showing an effect by a carbon concentration measurement method according an embodiment of the present invention.

FIG. 3 is a graph showing the effect of the method of measuring the carbon concentration according to the embodiment of the present invention. In FIG. 3, the abscissa represents the carbon concentration, and the ordinate represents the luminescence intensity ratio. In FIG. 3, the data given by [irradiation dose $1\times10^{15}$, low[Oi]] was obtained for silicon wafers having oxygen concentrations equal to or higher than $3.5\times10^{17}$ atoms/cm$^3$ and lower than $8.0\times10^{17}$ atoms/cm$^3$ (ASTM '79) with the electron irradiation dose of $1\times10^{15}$ electrons/cm$^2$. The data given by [irradiation dose $1\times10^{15}$, high[Oi]] was obtained for silicon wafers having oxygen concentrations of $8.0\times10^{17}$ atoms/cm$^3$ to $1.1\times10^{18}$ atoms/cm$^3$ (ASTM '79) with the electron irradiation dose of $1\times10^{15}$ electrons/cm$^2$. The data given by [irradiation dose $7\times10^{16}$, low[Oi]] was obtained for silicon wafers having oxygen concentrations equal to or higher than $3.5\times10^{17}$ atoms/cm$^3$ and lower than $8.0\times10^{17}$ atoms/cm$^3$ (ASTM '79) with the electron irradiation dose of $7\times10^{16}$ electrons/cm$^2$. The data given by [irradiation dose $7\times10^{16}$, high[Oi]] was obtained for silicon wafers having oxygen concentrations of $8.0\times10^{17}$ atoms/cm$^3$ to $1.1\times10^{18}$ atoms/cm$^3$ (ASTM '79) with the electron irradiation dose of $7\times10^{16}$ electrons/cm$^2$.

Referring to FIG. 3, the data given by [irradiation dose $1\times10^{15}$, low[Oi]] and the data given by [irradiation dose $1\times10^{15}$, high[Oi]] were obtained when the silicon wafers were irradiated with the electron beams at irradiation doses which were not optimized. On the other hand, the data given by [irradiation dose $7\times10^{16}$, low[Oi]] and the data given by [irradiation dose $7\times10^{16}$, high[Oi]] were obtained when the silicon wafers were irradiated with the electron beams at irradiation doses which were optimized. As will be apparent from FIG. 3, when the irradiation doses are not optimized, the slope of a straight line obtained from only data for the silicon wafers having low oxygen concentrations and the slope of a straight line obtained from only data for the silicon wafers having high oxygen concentrations have a relatively large difference. To the contrary, when the irradiation doses are optimized, the difference between the slopes is very small. That is, in the latter case, the influence of the oxygen concentration on the relationship between the carbon concentration and the luminescence intensity ratio is small. Therefore, the carbon concentration can be measured with a smaller number of calibration curves.

As described in Jpn. Pat. Appin. KOKAI Publication No. 2015-101529, both the luminescence intensity ratio and the oxygen concentration must be measured to obtain the carbon concentration of the silicon wafer for measurement. To the contrary, according to this measurement method, the influence of the oxygen concentration on the measurement result of the carbon concentration can be eliminated. For this reason, if the luminescence intensity ratio by the PL method is acquired, the carbon concentration can be obtained without measurement of the oxygen concentration and the like.

According to this manufacturing method, the above defective/nondefective determination can be performed at a predetermined frequency. In this case, when a wafer product whose impurity concentration exceeds an upper limit is manufactured, investigations of the causes of a high carbon concentration and the abnormality in the manufacturing process can be started immediately. This makes it possible to decrease a possibility of manufacturing a large number of wafer products whose carbon concentrations exceed the allowable range, thereby increasing the yield.

Working examples of the present invention will now be described.

<Determination of Calibration Curve>

Example 1

Silicon wafers No. 1 to No. 12 were prepared from a plurality of silicon single-crystal ingots produced by the Czochralski method. The carbon concentrations and the oxygen concentrations of these silicon wafers No. 1 to No. 12 were measured. The carbon concentrations were measured by the SIMS method, and the oxygen concentrations were measured by the FT-IR method. The measurement results are shown in Table 1 below.

TABLE 1

| No. | Carbon concentration [atoms/cm$^3$] | Oxygen concentration [atoms/cm$^3$] (ASTM '79) |
|---|---|---|
| 1 | $1.3 \times 10^{15}$ | $5.6 \times 10^{17}$ |
| 2 | $5.5 \times 10^{14}$ | $3.8 \times 10^{17}$ |
| 3 | $6.4 \times 10^{14}$ | $3.6 \times 10^{17}$ |
| 4 | $1.0 \times 10^{15}$ | $3.0 \times 10^{17}$ |
| 5 | $2.7 \times 10^{15}$ | $3.3 \times 10^{17}$ |
| 6 | $2.8 \times 10^{15}$ | $8.5 \times 10^{17}$ |
| 7 | $1.8 \times 10^{15}$ | $1.0 \times 10^{18}$ |
| 8 | $1.6 \times 10^{15}$ | $1.0 \times 10^{18}$ |
| 9 | $1.4 \times 10^{15}$ | $1.0 \times 10^{18}$ |
| 10 | $5.6 \times 10^{14}$ | $1.5 \times 10^{18}$ |
| 11 | $6.6 \times 10^{14}$ | $1.3 \times 10^{18}$ |
| 12 | $6.5 \times 10^{14}$ | $1.1 \times 10^{18}$ |

Based on the above measurement results, the silicon wafers No. 1 to No. 12 were classified into a first wafer group including the silicon wafers No. 1 to No. 5 having low oxygen concentrations and a second wafer group including the silicon wafers No. 6 to No. 12 having high oxygen concentrations.

Four calibration determination samples each having a size of 5 mm×10 mm were cut out from the central portion of each of the silicon wafers No. 1 to No. 12.

These calibration curve determination samples were irradiated with electron beams. Out of the four calibration curve determination samples obtained from each of the silicon wafers No. 1 to No. 12, the first sample was irradiated with an electron beam at an irradiation dose of $1 \times 10^{15}$ electrons/cm$^2$, the second sample was irradiated with an electron beam at an irradiation dose of $7 \times 10^{15}$ electrons/cm$^2$, the third sample was irradiated with an electron beam at an irradiation dose of $2 \times 10^{16}$ electrons/cm$^2$, and the fourth sample was irradiated with an electron beam at an irradiation dose of $7 \times 10^{16}$ electrons/cm$^2$.

The electron beam irradiation at the irradiation dose of $1 \times 10^{15}$ electrons/cm$^2$ was performed at a voltage of 2 MeV while air-cooling in the atmosphere such that the sample temperature did not exceed 100° C. The electron beam irradiation at the irradiation dose of $7 \times 10^{15}$ electrons/cm$^2$ was performed at a voltage of 1 MeV while water-cooling the irradiation table in the atmosphere such that the sample temperature did not exceed 100° C. Thus, carbon in each calibration curve determination sample was luminescence-activated.

Then, the luminescence intensities were measured by the PL method. This measurement was performed for all the calibration curve determination samples under the same conditions. More specifically, an excitation laser beam having a wavelength of 532 nm was used, and the intensity on each sample surface was set to 100 mW. Each calibration curve determination sample was immersed in liquid helium, and the FE luminescence intensity and the G-line luminescence intensity of each sample were measured while each sample was kept at a temperature of 4.2 K. Each ratio of these luminescence intensities (G/FE luminescence intensity) was obtained. The measurement results are shown in Table 2.

TABLE 2

| Group | Silicon wafer No. | G/FE luminescence intensity Electron beam irradiation dose [electrons/cm$^2$] | | | |
|---|---|---|---|---|---|
| | | $1 \times 10^{15}$ | $7 \times 10^{15}$ | $2 \times 10^{16}$ | $7 \times 10^{16}$ |
| 1st wafer group | 1 | $7.7 \times 10^{-1}$ | $1.3 \times 10^{0}$ | $3.3 \times 10^{0}$ | $4.5 \times 10^{0}$ |
| | 2 | $3.2 \times 10^{-1}$ | $4.8 \times 10^{-1}$ | $5.9 \times 10^{-1}$ | $4.0 \times 10^{-1}$ |
| | 3 | $4.8 \times 10^{-1}$ | $6.7 \times 10^{-1}$ | $9.2 \times 10^{-1}$ | $8.0 \times 10^{-1}$ |
| | 4 | $6.0 \times 10^{-1}$ | $1.2 \times 10^{0}$ | $2.6 \times 10^{0}$ | $2.4 \times 10^{0}$ |
| | 5 | $1.3 \times 10^{0}$ | $3.5 \times 10^{0}$ | $9.7 \times 10^{0}$ | $1.7 \times 10^{1}$ |
| 2nd wafer group | 6 | $1.4 \times 10^{0}$ | $2.8 \times 10^{0}$ | $1.0 \times 10^{1}$ | $3.9 \times 10^{1}$ |
| | 7 | — | $6.5 \times 10^{-1}$ | $1.7 \times 10^{0}$ | $3.8 \times 10^{0}$ |
| | 8 | $4.6 \times 10^{-1}$ | $6.8 \times 10^{-1}$ | $2.0 \times 10^{0}$ | $8.8 \times 10^{0}$ |
| | 9 | $1.9 \times 10^{-1}$ | $5.1 \times 10^{-1}$ | $1.7 \times 10^{0}$ | $2.1 \times 10^{0}$ |
| | 10 | $3.4 \times 10^{-2}$ | $5.4 \times 10^{-2}$ | $1.6 \times 10^{-1}$ | $3.8 \times 10^{-1}$ |
| | 11 | $5.5 \times 10^{-2}$ | $1.6 \times 10^{-1}$ | $3.4 \times 10^{-1}$ | $9.0 \times 10^{-1}$ |
| | 12 | $3.6 \times 10^{-2}$ | $1.2 \times 10^{-1}$ | $3.5 \times 10^{-1}$ | $3.0 \times 10^{-1}$ |

The luminescence intensity ratios thus obtained were classified into a plurality of data sets having different electron beam irradiation doses for each wafer group. A first calibration curve representing the relationship between the luminescent intensity ratio and the carbon concentration was determined for each data set, thereby obtaining calibration curve groups shown in FIGS. 4 to 7.

Figure 4:
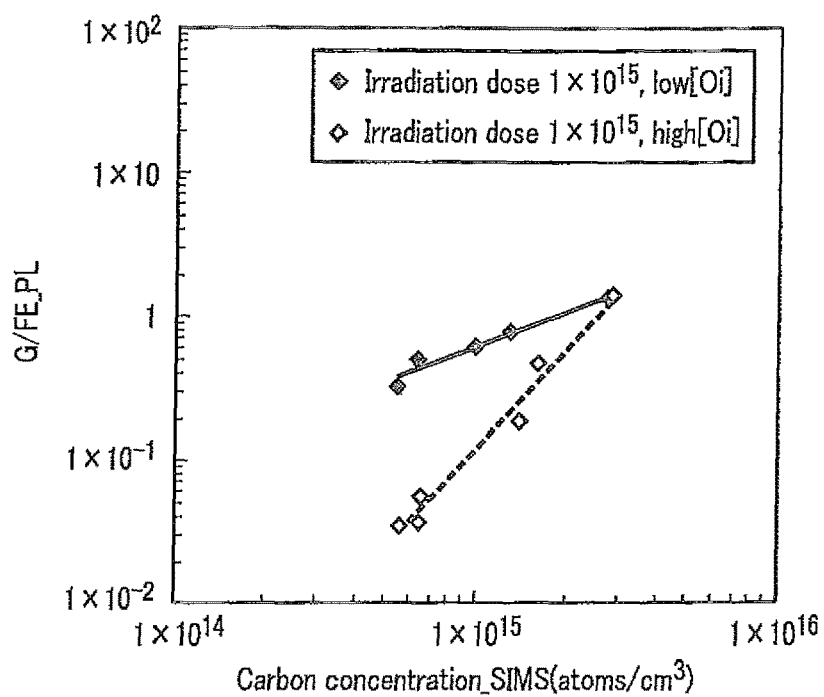
FIG. 4 is a log-log plot showing an example of a relationship between a carbon concentration and a luminescence intensity ratio when a calibration curve determination sample is irradiated with an electron beam at an irradiation dose of $1 \times 10^{15}$ electrons/cm$^2$.
Figure 5:
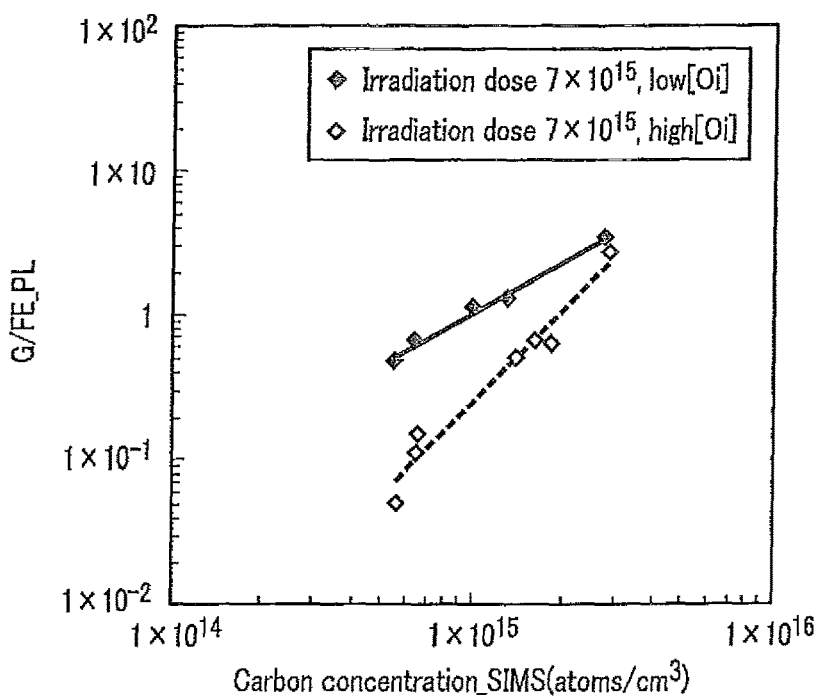
FIG. 5 is a log-log plot showing an example of a relationship between a carbon concentration and a luminescence intensity ratio when a calibration curve determination sample is irradiated with an electron beam at an irradiation dose of $7 \times 10^{15}$ electrons/cm$^2$.

FIG. 4 shows a log-log plot showing an example of the relationship between the carbon concentration and the luminescence intensity ratio when each calibration curve determination sample was irradiated with an electron beam at the irradiation dose of $1 \times 10^{15}$ electrons/cm$^2$. FIG. 5 shows a log-log plot showing an example of the relationship between the carbon concentration and the luminescence intensity ratio when each calibration curve determination sample was irradiated with an electron beam at the irradiation dose of $7 \times 10^{15}$ electrons/cm$^2$. FIG. 6 shows a log-log plot showing an example of the relationship between the carbon concentration and the luminescence intensity ratio when each calibration curve determination sample was irradiated with an electron beam at the irradiation dose of $2 \times 10^{16}$ electrons/cm$^2$. FIG. 7 shows a graph showing an example of the relationship between the carbon concentration and the luminescence intensity ratio when each calibration curve determination sample was irradiated with an electron beam at the irradiation dose of $7 \times 10^{16}$ electrons/cm$^2$.

In FIGS. 4 to 7, the abscissa represents the carbon concentration, and the ordinate represents the luminescence intensity ratio. Also, in FIGS. 4 to 7, a solid line represents the first calibration curve obtained for the first wafer group. A broken line represents the first calibration curve obtained for the second wafer group.

Figure 8:
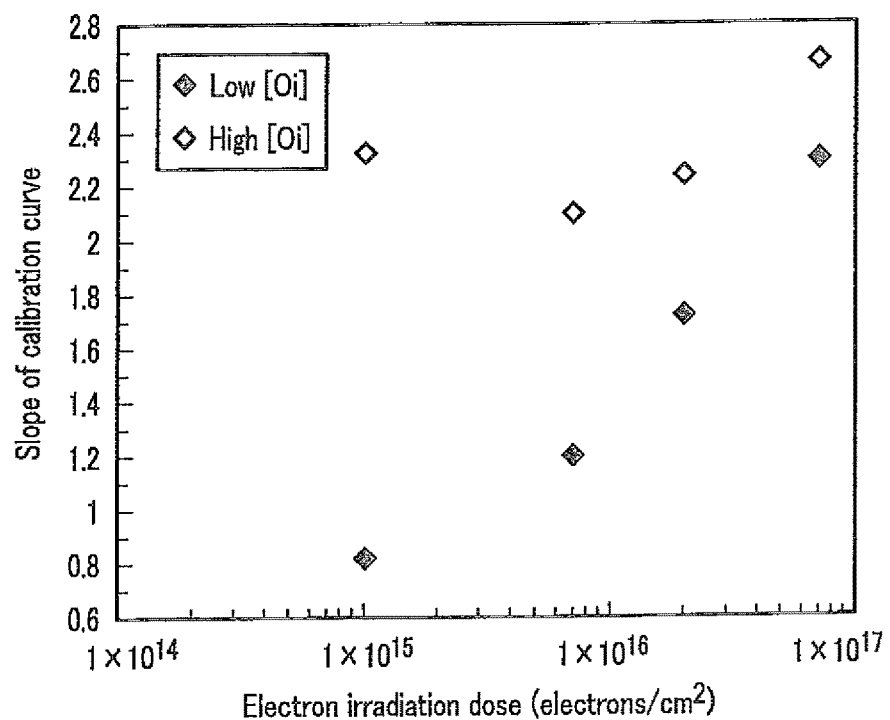
FIG. 8 is a semi-log plot showing an example of a relationship between an electron beam irradiation dose and a difference in slope between a pair of first calibration curves.

A slope was obtained for each of the resultant first calibration curves. The result is shown in Table 3. In addition, the result obtained by plotting the slopes of the first calibration curves with respect to the logs of the electron beam irradiation doses is shown in FIG. 8.

TABLE 3

| | Electron beam irradiation dose [electrons/cm$^2$] | | | |
|---|---|---|---|---|
| | $1 \times 10^{15}$ | $7 \times 10^{15}$ | $2 \times 10^{16}$ | $7 \times 10^{16}$ |
| Slope of 1st calibration curve (1st wafer group) | 0.82 | 1.2 | 1.7 | 2.3 |

TABLE 3-continued

| | Electron beam irradiation dose [electrons/cm$^2$] | | | |
|---|---|---|---|---|
| | $1 \times 10^{15}$ | $7 \times 10^{15}$ | $2 \times 10^{16}$ | $7 \times 10^{16}$ |
| Slope of 1st calibration curve (2nd wafer group) | 2.3 | 2.1 | 2.3 | 2.7 |

FIG. 8 is a semilog plot showing an example of the relationship between the electron beam irradiation dose and the difference in slope between the pair of first calibration curves. In FIG. 8, the abscissa represents the log of the electron beam irradiation dose, and the ordinate represents the slope of the calibration curve.

For each of the calibration curve groups each including a pair of first calibration curves equal to each other in the electron beam dose and different from each other in the oxygen concentration, a difference between the slopes of the paired first calibration curves included in the calibration curve group was obtained using the data in Table 3 and FIG. 8. As will be apparent from Table 3 and FIG. 8, when the electron beam irradiation dose was $7 \times 10^{16}$ electrons/cm$^2$, the above difference was 0.5 or less. Thus, the irradiation dose of $7 \times 10^{16}$ electrons/cm$^2$ was determined as the electron beam irradiation dose for measurement. Note that the difference between the slopes of the first calibration curves obtained when each sample was irradiated with an electron beam at the irradiation dose of $7 \times 10^{16}$ electrons/cm$^2$ was 0.38.

Out of the data sets used to determine the first calibration curves, the data sets whose electron beam irradiation dose was $7 \times 10^{16}$ electrons/cm$^2$ were selected, and using all the data included in the selected data sets, the relationship between the luminescence intensity ratios and the carbon concentrations was plotted on a log-log graph. The second calibration curve shown in FIG. 9 was obtained from the plotted data.

Figure 9:
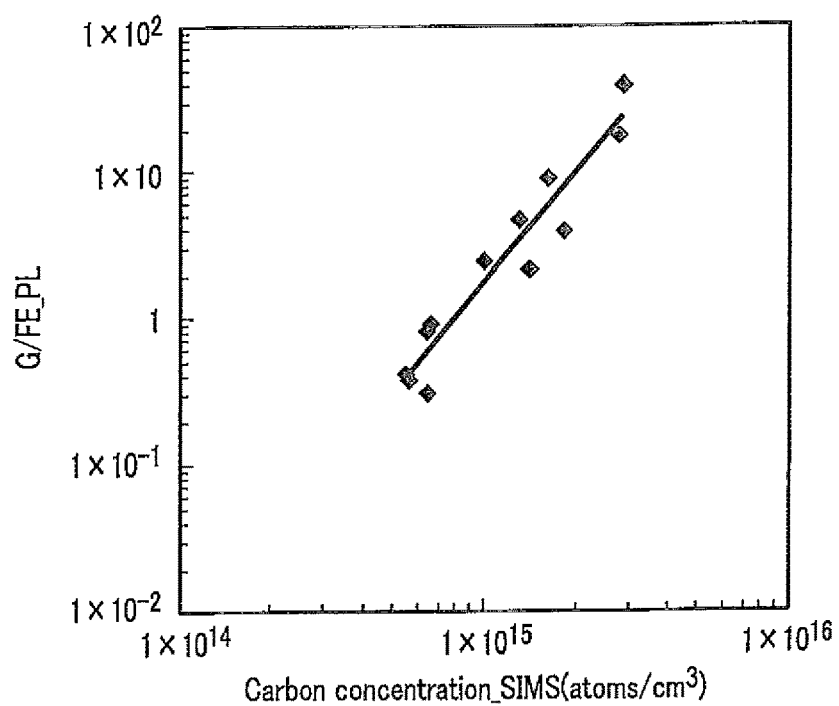
FIG. 9 is a log-log plot showing an example of a second calibration curve according to Example 1.

FIG. 9 is a log-log plot showing an example of the second calibration curve according to Example 1. In FIG. 9, the abscissa represents the carbon concentration, and the ordinate represents the luminescence intensity ratio.

The second calibration curve shown in FIG. 9 is a straight line represented by $y = 5 \times 10^{-38} x^{2.50}$ where x represents the carbon concentration and y represents the luminescence intensity ratio.

The correlation coefficient between the carbon concentration and the luminescence intensity ratio was obtained from all the data used to derive the second calibration curve. As a result, $R^2$ was 0.91, and thus a high correlation was found between the carbon concentration and the luminescence intensity ratio.

Comparative Example 1

The electron beam irradiation dose for measurement was determined as $1 \times 10^{15}$ electrons/cm$^2$. Using all the data included in the data sets whose electron beam irradiation dose was $1 \times 10^{15}$ electrons/cm$^2$ in Example 1, the relationship between the luminescence intensity ratios and the carbon concentrations was plotted on a log-log graph. The second calibration curve shown in FIG. 10 was obtained from these data. FIG. 10 is a log-log plot showing an example of the second calibration line according to Comparative Example 1. In FIG. 10, the abscissa represents the carbon concentration, and the ordinate represents the luminescence intensity ratio. The second calibration curve is a straight line represented by $y = 6 \times 10^{-26} x^{1.64}$.

When the correlation coefficient between the carbon concentration and the luminescence intensity ratio was obtained from all the data used to derive this second calibration curve, $R^2$ was 0.53.

Comparative Example 2

The electron beam irradiation dose for measurement was determined as $1 \times 10^{15}$ electrons/cm$^2$. Using all the data obtained for the first wafer group out of the data included in the data sets whose electron beam irradiation dose was $1 \times 10^{15}$ electrons/cm$^2$ in Example 1, the relationship between the luminescence intensity ratios and the carbon concentrations was plotted on a log-log graph. The second calibration curve for a low oxygen concentration indicated by a solid line in FIG. 4 was obtained.

The electron beam irradiation dose for measurement was determined as $1 \times 10^{15}$ electrons/cm$^2$. Using all the data obtained for the second wafer group out of the data included in the data sets whose electron beam irradiation dose was $1 \times 10^{15}$ electrons/cm$^2$ in Example 1, the relationship between the luminescence intensity ratios and the carbon concentrations was plotted on a log-log graph. The second calibration curve for a high oxygen concentration indicated by a broken line in FIG. 4 was obtained.

The second calibration curve for the low oxygen concentration is a straight line represented by $y = 3 \times 10^{-13} x^{0.821}$. The second calibration curve for the high oxygen concentration is a straight line represented $y = 1 \times 10^{-36} x^{2.33}$.

<Evaluation>

Silicon wafers A to F whose carbon concentrations were unknown were prepared from a plurality of silicon single-crystal ingots produced by the Czochralski method. Of the silicon wafers A to F, the silicon wafers A to C contained oxygen at low concentrations, while the silicon wafers D to F contained oxygen at high concentrations. Three measurement samples each having a size of 5 mm×10 mm were cut out from the central portion of each of the silicon wafers A to F.

One of the three measurement samples obtained from each wafer was irradiated with an electron beam at an irradiation dose of $7 \times 10^{16}$ electrons/cm$^2$, and the luminescence intensity ratio was obtained using the PL method under the same conditions as in the determination of the first calibration curve in Example 1. The luminescence intensity ratio thus obtained was referred to the second calibration curve determined in Example 1, thereby obtaining a carbon concentration.

Another one of the three measurement samples obtained from each of the silicon wafers A to F was irradiated with an electron beam at an irradiation dose of $1 \times 10^{15}$ electrons/cm$^2$, and the luminescence intensity ratio was obtained using the PL method under the same conditions as in the determination of the first calibration curve in Example 1. For each of the silicon wafers A to F, the luminescence intensity ratio thus obtained was referred to the second calibration curve determined in Comparative Example 1, thereby obtaining a carbon concentration.

For each of the silicon wafers A to C, the luminescence intensity ratio was referred to the second calibration curve for the low oxygen concentration determined in Comparative Example 2, thereby obtaining a carbon concentration. In addition, for each of the silicon wafers D to F, the luminescence intensity ratio was referred to the second calibration curve for the high oxygen concentration determined in Comparative Example 2, thereby obtaining a carbon concentration.

For the remaining one of the three measurement samples obtained from each wafer, a carbon concentration was measured by the SIMS method and an oxygen concentration was measured by the FT-IR method.

The results are shown in Table 4.

TABLE 4

| Wafer | A | B | C | D | E | F |
|---|---|---|---|---|---|---|
| G/FE luminescence intensity at irradiation dose of $7 \times 10^{16}$ electrons/cm$^2$ | $3.4 \times 10^0$ | $1.7 \times 10^1$ | $4.0 \times 10^{-1}$ | $6.0 \times 10^{-1}$ | $9.3 \times 10^0$ | $2.5 \times 10^1$ |
| Carbon concentration obtained using calibration curve of Example 1 (atoms/cm$^3$) | $1.4 \times 10^{15}$ | $2.6 \times 10^{15}$ | $5.8 \times 10^{14}$ | $6.8 \times 10^{14}$ | $2.0 \times 10^{15}$ | $3.0 \times 10^{15}$ |
| G/FE luminescence intensity at irradiation dose of $1 \times 10^{15}$ electrons/cm$^2$ | $1.0 \times 10^0$ | $1.2 \times 10^0$ | $3.1 \times 10^{-1}$ | $4.1 \times 10^{-2}$ | $5.3 \times 10^{-1}$ | $1.5 \times 10^0$ |
| Carbon concentration obtained using calibration curve of Comparative example 1 (atoms/cm$^3$) | $2.4 \times 10^{15}$ | $2.7 \times 10^{15}$ | $1.2 \times 10^{15}$ | $3.4 \times 10^{14}$ | $1.6 \times 10^{15}$ | $3.1 \times 10^{15}$ |
| Carbon concentration obtained using calibration curve for low oxygen concentration (atoms/cm$^3$) | $1.8 \times 10^{15}$ | $2.2 \times 10^{15}$ | $4.2 \times 10^{14}$ | — | — | — |
| Carbon concentration obtained using calibration curve for high oxygen concentration (atoms/cm$^3$) | — | — | — | $7.2 \times 10^{14}$ | $2.2 \times 10^{15}$ | $3.4 \times 10^{15}$ |
| Carbon concentration by SIMS (atoms/cm$^3$) | $1.4 \times 10^{15}$ | $2.6 \times 10^{15}$ | $5.5 \times 10^{14}$ | $7.5 \times 10^{14}$ | $1.7 \times 10^{15}$ | $3.0 \times 10^{15}$ |
| Oxygen concentration (atoms/cm$^3$) (ASTM' 79) | $3.2 \times 10^{17}$ | $5.4 \times 10^{17}$ | $6.0 \times 10^{17}$ | $9.3 \times 10^{17}$ | $1.2 \times 10^{18}$ | $1.5 \times 10^{18}$ |

As shown in Table 4, the carbon concentrations obtained by the process including irradiating with an electron beam at the irradiation dose determined in Example 1 and referring to the second calibration curve determined in Example 1 almost matched the carbon concentrations measured by the SIMS method regardless of the oxygen concentrations. This demonstrated that the carbon concentration could be measured using only one calibration curve regardless of the oxygen concentration when the second calibration curve was used.

On the other hand, the carbon concentrations obtained by the process including irradiating with an electron beam at the irradiation dose determined in Comparative Example 1 and referring to the second calibration curve determined in Comparative Example 1 largely differed from the carbon concentrations measured by the SIMS method. This demonstrated that it was difficult to accurately measure the carbon concentration of a silicon wafer containing oxygen, for example, at a high concentration by using only the second calibration curve of Comparative Example 1.

When the carbon concentrations of silicon wafers A to C were obtained with reference to, for example, the second calibration curve for the low oxygen concentration, the carbon concentrations thus obtained had small differences from the results of the carbon concentration measurements by SIMS. On the other hand, when the carbon concentration of the silicon wafer D was obtained with reference to the second calibration curve for the low oxygen concentration, the resultant value had a large difference from the result of the carbon concentration measurement by SIMS.

Similarly, when the carbon concentrations of the silicon wafers D to F were obtained with reference to the second calibration curve for the high oxygen concentration, differences from the results of the carbon concentration measurements by SIMS were small. However, when the carbon concentration of, for example, the silicon wafer C was obtained with reference to the second calibration curve for the high oxygen concentration, the resultant value had a large difference from the result of the carbon concentration measurement by SIMS.

When the electron beam irradiation dose was not optimized, a calibration curve had to be determined for each oxygen concentration as in the second calibration curve determined in Comparative Example 2 in order to accurately measure a carbon concentration.

The present invention is not limited to the above embodiments described above and can be variously modified without departing from the scope of the present invention in the implementation stage. Embodiments can be combined variously and practiced. In this case, an effect of a combination can be obtained. In addition, the above embodiments include various inventions, and various inventions can be extracted by combinations selected from the plurality of disclosed constituent elements. For example, the problem can be solved even if some constituent elements are omitted from all the constituent elements disclosed in the embodiments. If an effect can be obtained, an arrangement from which constituent elements are omitted can be extracted as an invention.

What is claimed is:

1. A calibration curve determination method comprising:
    a first step of providing a plurality of wafer groups each including a plurality of silicon wafers having the same oxygen concentration and different carbon concentrations, the wafer groups being different from each other in the oxygen concentration of the silicon wafers included therein;
    a second step of irradiating a plurality of regions of each of the silicon wafers included in each of the wafer groups with electron beams at different irradiation doses;
    a third step of obtaining, by a photoluminescence method, an intensity ratio of a first luminescence intensity deriving from silicon to a second luminescence intensity deriving from carbon for each of the regions irradiated with the electron beams;
    a fourth step of classifying a plurality of data each including the oxygen concentration, the carbon concentration, the irradiation dose, and the intensity ratio into a plurality of data sets, the data included in each of the data sets having the same irradiation dose and the same oxygen concentration, and the data sets being different from each other in at least one of the irradiation dose and the oxygen concentration, and determining a first calibration curve representing a relationship between the intensity ratio and the carbon concentration for each of the data sets to obtain a calibration curve group;

a fifth step of selecting one or more combinations from the calibration curve group, each of the one or more combination being a pair of the first calibration curves which are equal to each other in the irradiation dose and different from each other in the oxygen concentration, and the one or more combinations being different from each other in the irradiation dose, and obtaining a difference between slopes of the paired first calibration curves on a log-log plot for each of the one or more combinations; and a sixth step including selecting a specific combination out of the one or more combinations, the specific combination having the difference between the slopes within a predetermined range or smaller than the difference between the slopes of one or more of other combinations, determining the irradiation dose in common to the first calibration curves of the specific combination as an electron beam irradiation dose for measurement, and determining a second calibration curve using all the data included in pair(s) of the data sets used to determine the pair(s) of first calibration curves included in at least the specific combination, the second calibration curve representing a relationship between the intensity ratio and the carbon concentration and being usable in combination with the electron beam irradiation dose for measurement.

2. The determination method of claim 1, wherein the carbon concentrations of the silicon wafers fall within a range of $4 \times 10^{14}$ to $4 \times 10^{15}$ atoms/cm$^3$ in each of the wafer groups.

3. The determination method of claim 1, wherein the oxygen concentrations of the silicon wafers fall within a range of $1 \times 10^{17}$ to $2 \times 10^{18}$ atoms/cm$^3$ (ASTM '79) in each of the wafer groups.

4. The determination method of claim 1, wherein the irradiation dose of the electron beam in the second step falls within a range of $1 \times 10^{14}$ to $1 \times 10^{18}$ electrons/cm$^2$.

5. The determination method of claim 1, wherein the slope difference in the sixth step is 0.5 or less.

6. The determination method of claim 1, wherein the sixth step further includes calculating a correlation coefficient between the carbon concentration and the intensity ratio from all the data included in the pair of the data sets used or to be used to determine the pair of first calibration curves included in the specific combination, and confirming that the second calibration curve can be used based on the correlation coefficient.

7. The determination method of claim 1, wherein in the sixth step, the second calibration curve is determined using all the data included in the pair of data sets and further using all the data included in one or more data sets, the irradiation dose of the one or more data sets being the same as that of the pair of data sets, and the oxygen concentration of the one or more data sets being between the oxygen concentration of one of the pair of data sets and the oxygen concentration of the other of the pair of data sets.

8. A carbon concentration measurement method comprising:

determining the electron beam irradiation dose for measurement and determining the second calibration curve by the determination method according to claim 1;

irradiating a silicon wafer for measurement whose carbon concentration is unknown with an electron beam at the electron beam irradiation dose for measurement;

obtaining, by a photoluminescence method, an intensity ratio of a first luminescence intensity deriving from silicon to a second luminescence intensity deriving from carbon for the silicon wafer for measurement irradiated with the electron beam; and referring the intensity ratio thus obtained to the second calibration curve to obtain a carbon concentration of the silicon wafer for measurement.

9. The measurement method according to claim 8, wherein dopant concentrations of the plurality of silicon wafers and the silicon wafer for measurement fall within a range in which the first luminescence intensity can be measured.

10. A silicon wafer-manufacturing method comprising measuring a carbon concentration in the silicon wafer for measurement by the measurement method according to claim 8.

* * * * *